US009244088B2

(12) United States Patent
Sakairi et al.

(10) Patent No.: US 9,244,088 B2
(45) Date of Patent: Jan. 26, 2016

(54) AUTOMATED ANALYZER

(71) Applicant: HITACHI HIGH-TECHNOLOGIES CORPORATION, Tokyo (JP)

(72) Inventors: Susumu Sakairi, Hitachinaka (JP); Taku Sakazume, Hitachinaka (JP); Katsuaki Takahashi, Hitachinaka (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 0 days.

(21) Appl. No.: 14/291,029

(22) Filed: May 30, 2014

(65) Prior Publication Data

US 2014/0271359 A1      Sep. 18, 2014

Related U.S. Application Data

(63) Continuation of application No. 13/145,355, filed as application No. PCT/JP2010/000212 on Jan. 18, 2010, now Pat. No. 8,753,572.

(30) Foreign Application Priority Data

Jan. 29, 2009   (JP) ................................ 2009-017462

(51) Int. Cl.
*G01N 35/10*   (2006.01)
*G01N 35/00*   (2006.01)

(52) U.S. Cl.
CPC ........ *G01N 35/1095* (2013.01); *G01N 35/1083* (2013.01); *G01N 35/0098* (2013.01); *Y10T 436/115831* (2015.01); *Y10T 436/119163* (2015.01)

(58) Field of Classification Search
CPC ............ Y10T 463/119163; Y10T 463/115831
USPC ...................................... 422/62–67
See application file for complete search history.

(56) References Cited

U.S. PATENT DOCUMENTS

| | | | |
|---|---|---|---|
| 6,019,945 A * | 2/2000 | Ohishi et al. | 422/65 |
| 2004/0241872 A1 | 12/2004 | Wegrzyn et al. | |
| 2004/0253146 A1 | 12/2004 | Shiba et al. | |
| 2005/0207938 A1 * | 9/2005 | Hanawa et al. | 422/64 |
| 2006/0286563 A1 | 12/2006 | Lin et al. | |

FOREIGN PATENT DOCUMENTS

| | | |
|---|---|---|
| EP | 0745855 | 12/1996 |
| JP | 213857 | 1/1990 |
| JP | 3262970 | 11/1991 |
| JP | 44274 | 1/1992 |

(Continued)

OTHER PUBLICATIONS

Machine-Translation of JP 2008058127A, Imai et al., (No Date).*

(Continued)

*Primary Examiner* — Jill Warden
*Assistant Examiner* — Julie Tavares
(74) *Attorney, Agent, or Firm* — Mattingly & Malur, PC

(57) ABSTRACT

Stepped portions of a flow channel are reduced by completely fixing the channel that extends to the measuring unit, and reducing connections in the channel, thereby to suppress a disturbance in the flow of the liquid suctioned into the measuring unit. A means is provided so that the reaction solution and reagent suctioned will move towards the channel through which the liquids are suctioned.

8 Claims, 8 Drawing Sheets

(56) References Cited

FOREIGN PATENT DOCUMENTS

| | | |
|---|---|---|
| JP | 5281243 | 10/1993 |
| JP | 610868 | 2/1994 |
| JP | 8-146010 A | 6/1996 |
| JP | 949847 | 2/1997 |
| JP | 9127126 | 5/1997 |
| JP | 1090278 | 4/1998 |
| JP | 10-267936 A | 10/1998 |
| JP | 10-300752 A | 11/1998 |
| JP | 11242032 | 9/1999 |
| JP | 11258237 | 9/1999 |
| JP | 2008058127 | 3/2008 |
| JP | 2008058127 A * | 3/2008 |

OTHER PUBLICATIONS

Japanese Office Action received in corresponding Japanese Application No. 2014-096448 dated May 19, 2015.

* cited by examiner

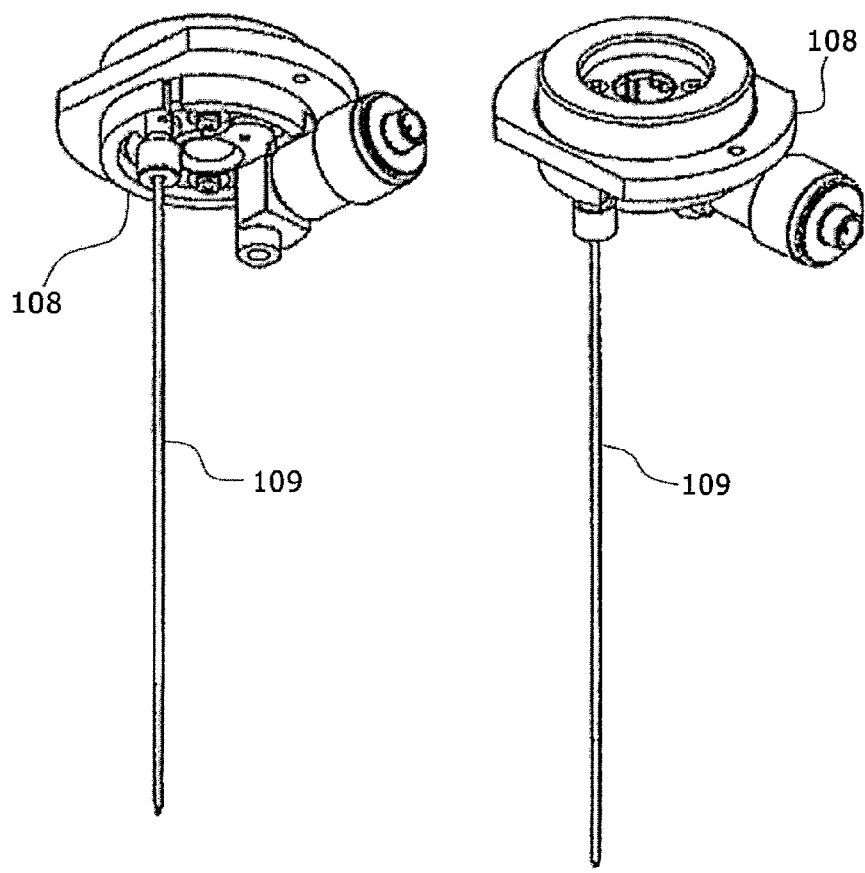

FIG.1-B
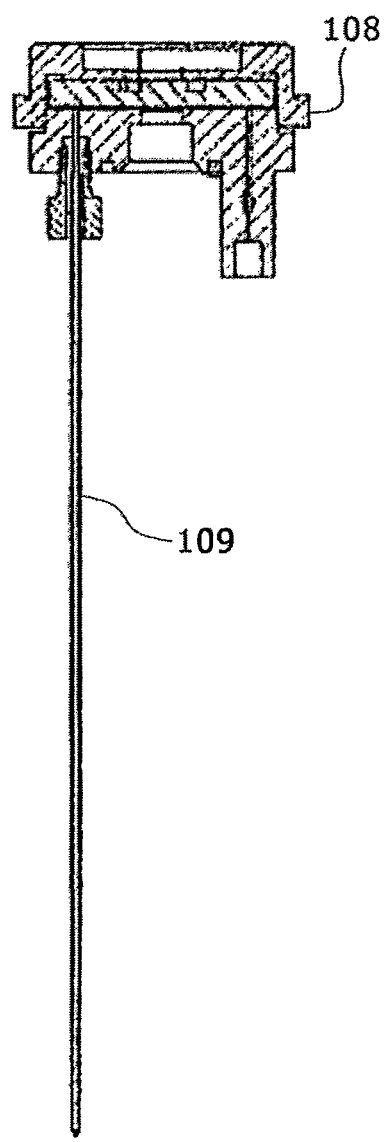

F I G . 2
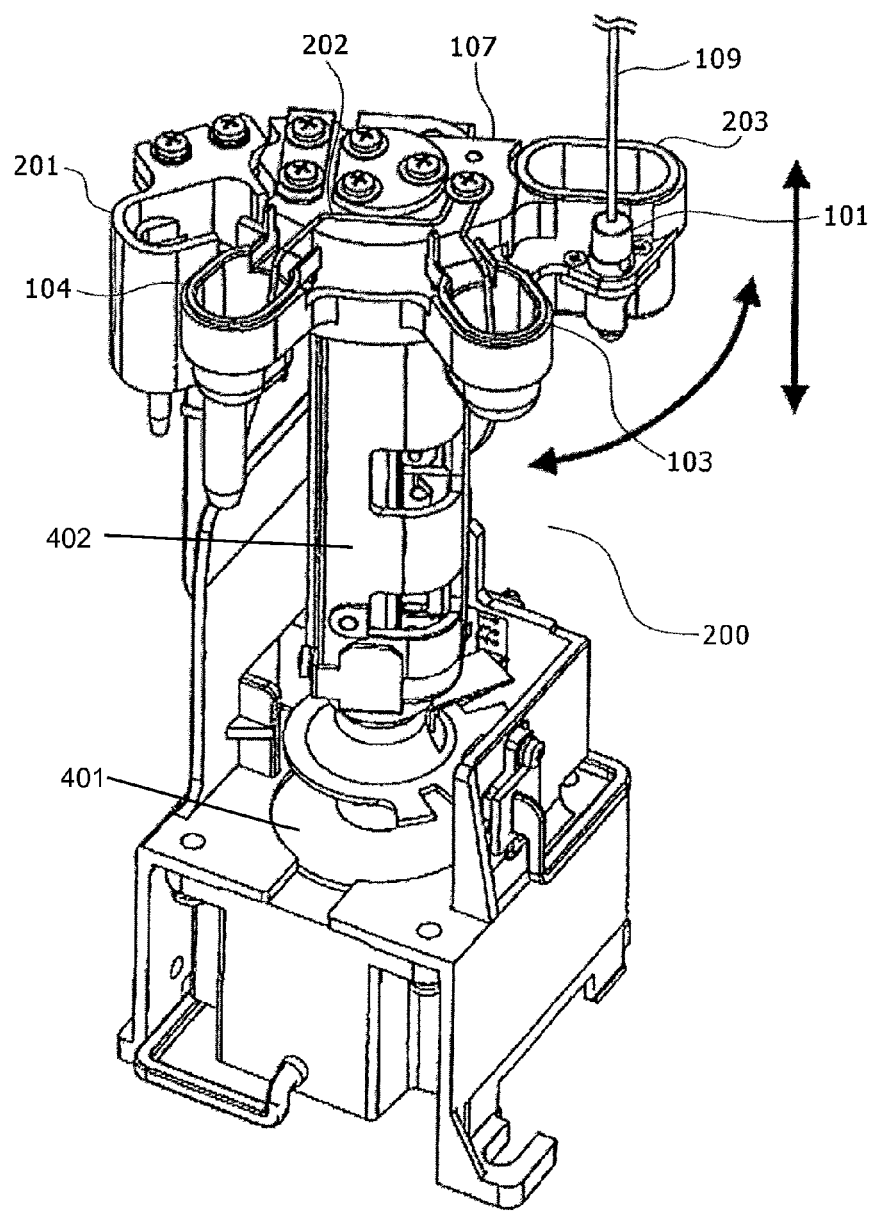

AUTOMATED ANALYZER

This is a continuation application of U.S. Ser. No. 13/145,355, filed Aug. 1, 2011, which is a 371 of PCT Application No. PCT/JP2010/000212, filed Jan. 18, 2010 and claims priority to JP 2009-017462, filed Jan. 29, 2009. The entire disclosures of all of these applications are hereby incorporated by reference.

TECHNICAL FIELD

The present invention relates to clinical examination and chemical analysis, and more particularly, to an automated analyzer that uses magnetic particles during analysis.

BACKGROUND ART

During immunoassay that uses a flow cell, automated analyzers, in particular, that employ magnetic particles quantitatively analyze constituents of a substance to be measured, by causing antigen-antibody reactions in a liquid mixture of a sample, magnetic particles, an antibody that binds the magnetic particles to a substance in the sample that is to be measured, and a labeled antibody including a labeled substance.

To ensure that constituents not to be measured are removed from the liquid mixture (hereinafter, referred to as the reaction solution) that contains the constituents to be measured, the magnetic particles, and the labeled substance, a magnetic separator such as a magnet is provided on a flow channel through which the reaction solution flows.

Because of their binding to the magnetic particles, the constituents to be measured are captured by the magnetic separator, but the constituents not to be measured flow intact without being captured. The constituents to be measured can therefore be separated from those which are not to be measured.

When a voltage is applied to the thus-separated constituents to be measured, the labeled substance that has bound to each of these constituents will emit light, so the quantity of constituents to be measured can be determined by measuring the amount of light emitted. Such an analyzer is described in Patent Document 1, for example.

PRIOR ART LITERATURE

Patent Document

Patent Document 1: JP-A-11-258237

SUMMARY OF THE INVENTION

Problems to be Solved by the Invention

Conventional immunoanalyzers have adopted a scheme in which a reaction solution and a reagent are placed in predefined positions and a nozzle for suctioning the liquids is moved to a predefined position. Constituent elements of the flow channel from a general nozzle structure to a measuring unit (flow cell) are as follows:

A metallic or any other form of nozzle free of deformation, a shape-variable tube connecting to the nozzle, a metallic temperature-control pipe connecting to the shape-variable tube, a shape-variable tube connecting to the temperature-control pipe, and a flow cell connecting to the latter shape-variable tube.

In the channel configuration, four channel connections exist: between the nozzle and the former shape-variable tube, between the former shape-variable tube and the temperature-control pipe, between the temperature-control pipe and the latter shape-variable tube, and between the latter shape-variable tube and the flow cell.

Channel connections are very difficult to completely match in channel inside diameter because of a fabrication error, and thus, these connections are usually stepped. The flow of the liquid is disturbed at the steps, and more particularly for a reaction solution that contains magnetic particles, the magnetic particles stop flowing at the steps and stay thereat or the flow of the particles is temporarily interrupted thereat. Additionally, these dwelling magnetic particles are pushed in a downstream direction by the flow of the liquid from an upstream direction and irregularly break away from the steps. It has been likely, therefore, that for example, if, during measurement of the sample, dwelling constituents of the reaction solution which was measured during the previous operation break away and begin to flow again, measurement errors due to a carryover will occur under the particular measuring conditions.

In addition, the nozzle itself that forms part of the channel has frequently moved to suction the reaction solution and the reagent, and during the movement, the shape-variable tube connected to the nozzle changes the shape to bend or expand/contract. Under specific conditions, this has likely to cause the problems that a change in the inside diameter of the tube during the measurement changes the state of the flow, that the flow of the magnetic particles is interrupted at bends, or that a smooth flow of the liquid in the channel is impeded by vibration during the movement of the nozzle.

Even if the nozzle suctions a reaction solution that contains magnetic particles of a uniformly dispersing nature, the presence of the differences in height between the channel connections and the occurrence of changes in channel state will cause nonuniform dispersion of the magnetic particles in the channel. Thus, when the magnetic particles are captured using magnetic separation means, the particles will not be capturable onto a capturing surface at a uniform magnetic-particles concentration, and even when light is emitted by applying a voltage, the amount of light detected will decrease in reproducibility. It is, therefore, desirable that the channel from the nozzle to the measuring unit be free of steps, smooth, and stable in channel state.

An object of the present invention is to provide an immunoanalyzer in which a measuring channel through which a reaction solution flows during measurement is free from deformation, bending, and expansion/contraction, the measuring channel being further constructed to implement uniform dispersion of constituents of the reaction solution in the channel.

Means for Solving the Problems

An automated analyzer configuration according to claim 1 of the present invention for achieving the above object is described below.

The automated analyzer comprises: a nozzle for suctioning a reaction solution generated by mixing a sample, magnetic particles, an antibody that binds the magnetic particles to a substance in the sample that is to be measured, and a labeled antibody including a labeled substance; magnetic separation means for capturing magnetic constituents contained in a reaction solution suctioned by the nozzle, in such a manner that only the magnetic constituents are captured to separate magnetic constituents and nonmagnetic constituents from each other; and a measuring unit for quantitatively determining the magnetic constituents captured by the magnetic separation means; wherein the nozzle is directly connected to the measuring unit.

In contrast to a conventional analyzer in which a shape-variable tube has been connected between a nozzle and a measuring unit during immunoassay with magnetic particles, the automated analyzer according to claim 1 is of a structure in which the nozzle and the measuring unit are directly interconnected so that a flow channel extending to the measuring unit maintains an original shape during measurement.

While the nozzle and measuring unit here may be integrally formed or may have a shape with both interconnected after being formed separately, a boundary between the nozzle and the measuring unit is desirably connected smoothly without a difference in height.

A reaction vessel that accommodates the reaction solution containing the substance to be measured, and a reagent vessel that accommodates the reagent required for the analysis are placed directly under the fixed nozzle. The nozzle sequentially suctions the reaction solution and the reagent and sends both to the measuring unit. Of the reaction solution that has been sent to the measuring unit, only the magnetic constituents containing the substance to be measured are captured by the magnetic separation means and the non-magnetic constituents are washed away by the reagent. In addition, after the measurement, another reagent is suctioned by the nozzle and completely washes away the magnetic constituents left in the measuring unit, thereby to get the measuring unit ready for next measuring operation.

The flow channel in this region is completely fixed and has a smoothly worked inner surface, so the reaction solution in both the channel and the measuring unit flows uniformly. Around the measuring unit, a magnetic separator that applies magnetism to the reaction solution is disposed to separate the constituents-to-be-measured that were bound to the magnetic particles from the reaction solution.

The magnetic separator may use a permanent magnet or any other suitable element for generating magnetism.

Applying the magnetic separator to the uniform flow of the reaction solution increases reproducibility of the measurement since magnetic particles stick to a capturing surface uniformly.

Effects of the Invention

As described above, according to the present invention, these features and characteristics ensure a stable flow in the measuring unit, even for magnetic particles whose flow is prone to interruptions or nonuniformity in a small-diameter channel, and reduce carryovers and nonuniformity of data analytical results.

Improvement of measurement results in reproducibility and in accuracy is thus anticipated.

BRIEF DESCRIPTION OF THE DRAWINGS

FIG. 1-A is an external view that shows connection of a flow cell and a nozzle;

FIG. 1-B is a sectional view that shows the connection of the flow cell and the nozzle;

FIG. 2 is an external view of the reaction solution/reagent transport mechanism;

FIG. 3-1 is a plan view of an automated analyzer, showing reaction vessel loading into/unloading from a reaction disk;

FIG. 3-2 is another plan view of the automated analyzer, showing reaction vessel loading into/unloading from the reaction solution/reagent transport mechanism;

FIG. 3-3 is yet another plan view of the automated analyzer, showing a reaction solution suctioning position;

FIG. 3-4 is a further plan view of the automated analyzer, showing a cleaning position for the nozzle;

FIG. 3-5 is a further plan view of the automated analyzer, showing a suction position for reagent (a) and a supply position for reagent (b);

FIG. 3-6 is a further plan view of the automated analyzer, showing a suction position for reagent (b) and a supply position for reagent (a); and FIG. 3-7 is a further plan view of the automated analyzer, showing a cleaning liquid suction position;

MODE FOR CARRYING OUT THE INVENTION

A nozzle is directed downward and connected directly to a flow cell. A reaction vessel for accommodating a reaction solution, reagent vessels each for accommodating a reagent, and other tools and appliances absolutely necessary for analysis are arranged on one surface, and then these articles are sequentially moved to a horizontal position directly under the nozzle. After this, each article is moved upward for the reaction solution and the reagents to be suctioned through the nozzle into the flow cell for measurement.

An embodiment of the present invention will be described hereunder using the accompanying drawings.

Figure 1:
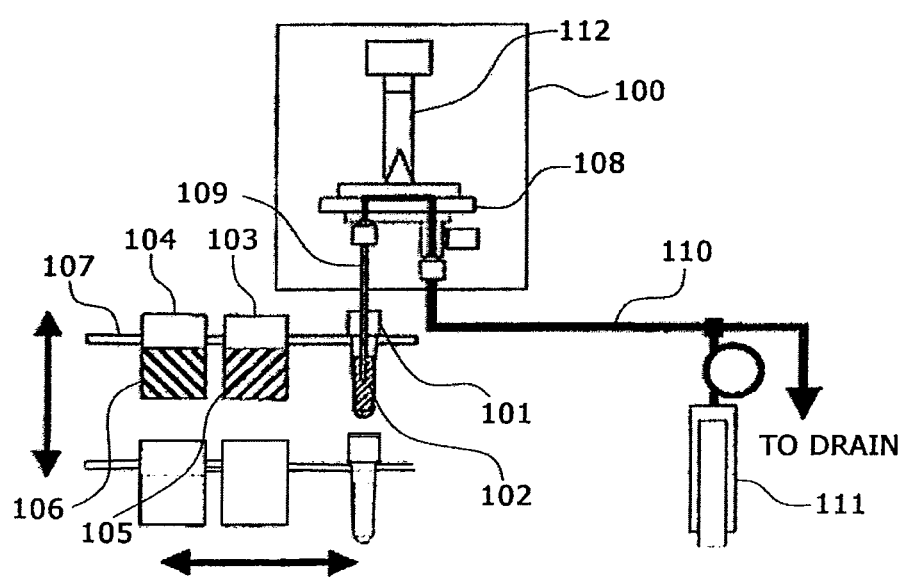
FIG. 1 is an illustrative diagram showing a basic configuration of measuring unit periphery and a reaction solution/reagent transport mechanism.

FIG. 1 shows a basic configuration of the present invention. A reaction solution 102 that contains a substance to be measured and magnetic particles each bound onto the substance, a reaction vessel 101 that accommodates the reaction solution 102, two kinds of reagents, (a) 105 and (b) 106, that are likewise necessary for measurement, reagent vessels (a) 103 and (b) 104 that accommodate the reagents (a) 105 and (b) 106, respectively, and a retainer 107 that retains the reaction vessel 101 and the reagent vessels (a) 103 and (b) 104, are basic constituent elements of a reaction solution/reagent transport mechanism. A flow cell 108, a nozzle 109 that connects to the flow cell 108, a tube 110 connected to the flow cell 108, and a syringe 111 connected to the tube 110 are basic constituent elements of measuring unit periphery. A region from the nozzle 109 to the syringe 111 forms one flow channel. The reaction solution/reagent transport mechanism has a horizontal transport mechanism 401 that moves the retainer 107 rotationally or linearly in a horizontal plane and a vertical transport mechanism 402 that move the retainer 107 vertically. The reaction solution/reagent transport mechanism moves the reaction solution 102 or reagent (a) 105, (b) 106 retained by the retainer 107, to the nozzle 109 in appropriate timing according to a particular measuring sequence. By suctioning the reaction solution 102 or the reagent (a) 105, (b) 106 using the nozzle 109 and syringe 111, the liquid moves to the flow cell 108. During the suctioning of the reaction solution 102, a magnetic separation means captures, inside the flow cell 108, a reaction product that includes the magnetic particles contained in the reaction solution 102. Applying a voltage to the captured reaction product makes the reaction product emit light. The amount of light emitted is detected by a photomultiplier (PMT) 112, so that the quantity of substance under measurement is determined. For more stable measurement results, it is desirable that when the magnetic separation means captures the reaction product inside the flow cell 108, the reaction product be captured uniformly onto a capturing surface. This can be performed by completely fixing the channel and reducing its connections. More specifically, the reaction product having a uniform concentration in the reaction solution 102 can be suctioned onto the internal capturing surface of the flow cell 108 without flow interruptions due to reasons such as a change in a shape of the channel or presence of steps between the connections, and maintain the uniform concentration. FIG. 1 shows an example in which the channel from the nozzle 109 to the flow cell 108 is completely fixed, but a connection is present in one place. In the present embodiment, the flow cell 108 and the nozzle 109 are formed as separate components to allow for ease in manufacture and maintainability (including nozzle replaceability and flow cell replaceability). An external view of the interconnected flow cell 108 and nozzle 109 is shown in FIG. 1-A. A sectional view of the interconnected flow cell 108 and nozzle 109 is shown in FIG. 1-B. The connection between the flow cell and the nozzle can be removed by integrating both into a single unit. Complete removal of the connection creates a more stable flow during suctioning. In addition, carryovers to next measurement are further reduced.

Figures 1, 3:
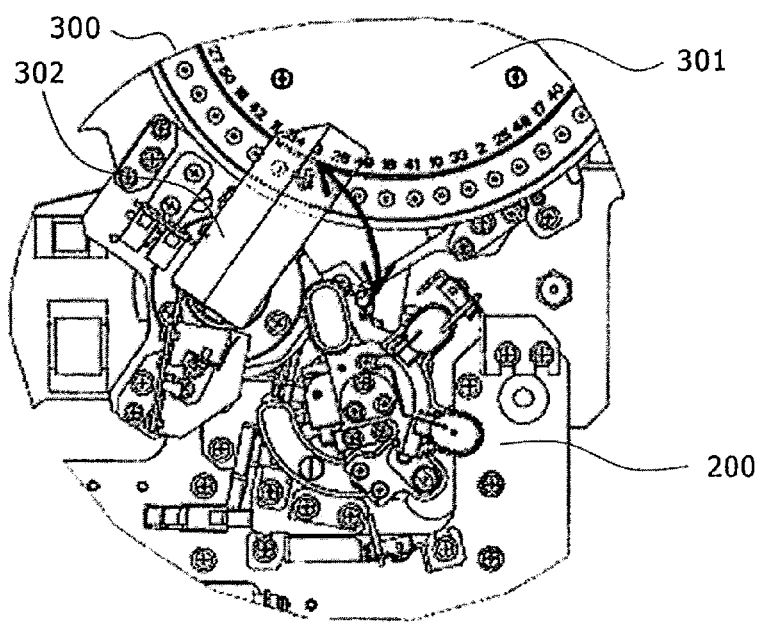
Figures 2, 3:
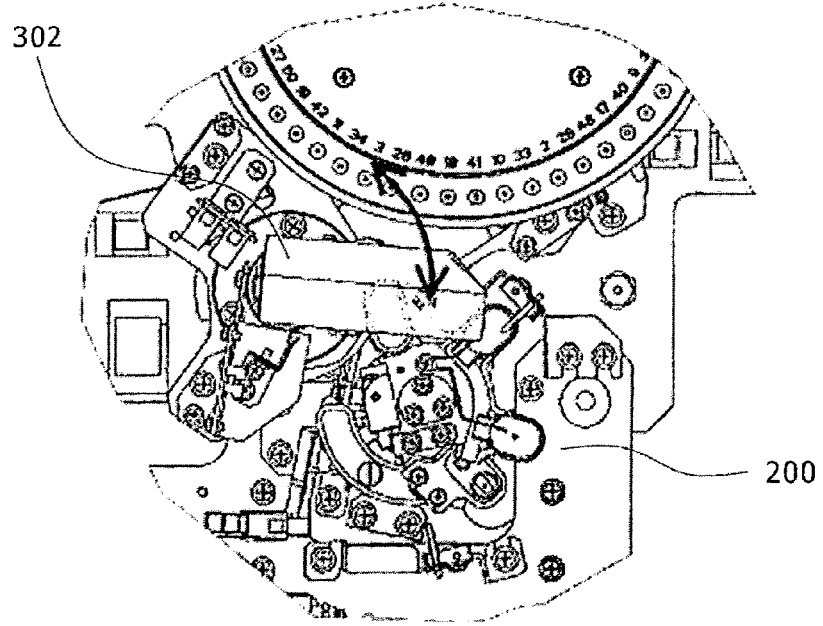
Figure 3:
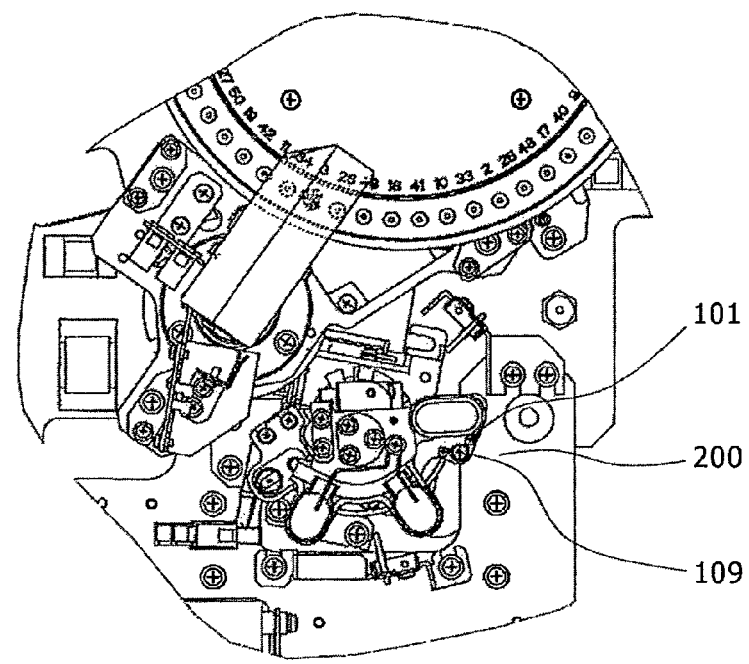

FIG. 2 is an external view of the reaction solution/reagent transport mechanism 200 of the present invention. The reaction solution/reagent transport mechanism 200 is disposed directly under the nozzle 109 connected to the measuring unit, and has mounting regions for the reaction vessel 101 and reagent vessels (a) 103, (b) 104, and for a nozzle-cleaning unit 201 in the retainer 107. Horizontal rotation of the retainer 107 in the appropriate timing according to the particular measuring sequence moves the mounting regions for the reaction vessel 101 and other elements to a position directly below the nozzle 109. After this, the retainer 107 moves upward to insert the nozzle 109 into the reaction vessel 101 or the reagent vessel (a) 103, (b) 104 and make the nozzle 109 suction the reaction solution 102 or the reagent (a) 105, (b) 106. Additionally after the suctioning of these liquids, the nozzle cleaning unit 201 moves to the position of the nozzle 109 in a similar manner to the reaction vessel 101 and other elements in appropriate timing in order to clean the nozzle 109, and jets cleaning water to clean the nozzle 109. In the present embodiment, the retainer 107 here rotates horizontally to move each mounting region within the retainer 107 to a position directly underneath the nozzle. The retainer, however, does not absolutely require rotational movement. Instead, the retainer 107 may be constructed, for example, to move linearly arranged mounting regions to a position directly below the nozzle 109, by linear, horizontal movement. In addition, while the present embodiment uses one movable retainer 107 to retain the reaction vessel 101, the reagent vessels (a) 103, (b) 104, and the nozzle cleaning unit 201, since the mounting regions for the reaction vessel 101 and other elements need only to be moved to the nozzle 109, the present invention can include a plurality of retainers 107 accessible to the nozzle 109, each of the retainers having one or a plurality of access positions with respect to the nozzle 109. Furthermore, although the present embodiment uses two kinds of reagents, (a) 105 and (b) 106, mounting locations for other additional reagents or the like may be provided according to particular needs. The present embodiment further includes a retaining region for a cleaning liquid vessel 203 to hold a channel-cleaning liquid for maintenance of the channel in the measuring unit. This retaining region is used for periodic (such as, weekly) maintenance and not used during routine analysis.

FIGS. 3-1 to 3-7 are plan views that cover periphery of the reaction solution/reagent transport mechanism 200 of the present invention, shown in FIG. 2, in examples of application to an automated analyzer 300, showing various stopping positions of the reaction solution/reagent transport mechanism 200 in rotational directions. In an actual configuration, a measuring mechanism 100 is disposed at an upper side of the reaction solution/reagent transport mechanism 200. For a better understanding of the drawing, however, illustration of the measuring mechanism 100 is omitted and only the nozzle 109 is shown.

To implement continuous measurement with the automated analyzer 300, the reaction vessel 101 accommodating the reaction solution 102 needs replacing for each measuring operation. A need also arises to provide an element that transports to the reaction solution/reagent transport mechanism 200 the reaction vessel 101 accommodating the reaction solution 102 which has been used for a reaction in a reaction disk 301, and an element that unloads from the reaction solution/reagent transport mechanism 200 the reaction vessel 101 that has been used for the measuring operation. In the present embodiment, a reaction vessel transport unit 302 transports the reaction vessel 101 between the reaction disk 301 and the reaction solution/reagent transport mechanism 200. The reaction disk 301 itself is of horizontally rotatable construction and moves the mounted reaction vessel 101 to a position at which the reaction vessel transport unit 302 can remove the reaction vessel 101 from the reaction disk 301. The reaction vessel transport unit 302 includes a device that grips the reaction vessel 101, and a device that moves the gripping device upward/downward, and has a structure that allows the devices to be moved horizontally. These devices and structure of the reaction vessel transport unit 302 move the reaction vessel 101 between the reaction disk 301 and the reaction solution/reagent transport mechanism 200, as shown in FIGS. 3-1 and 3-2.

Figures 3, 4:
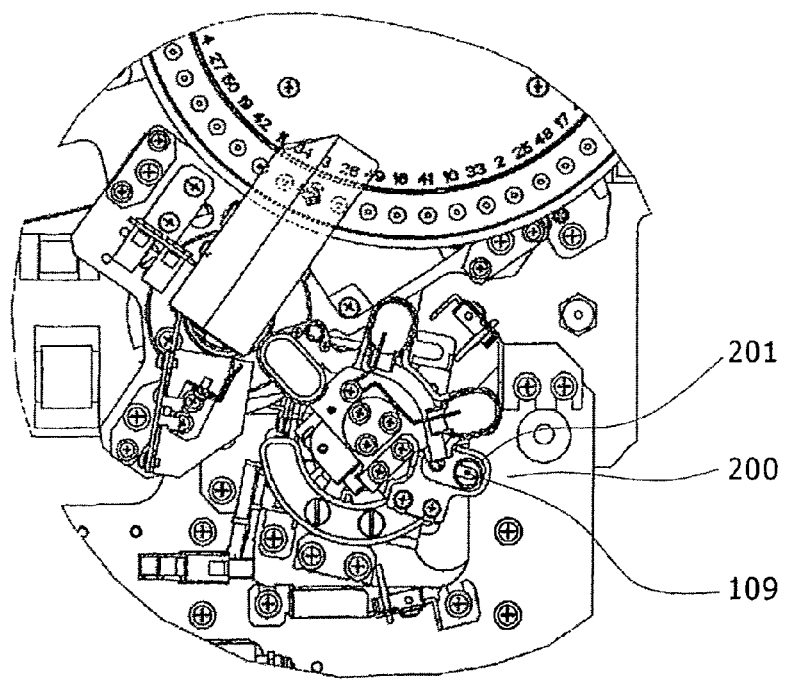

The transported reaction vessel 101 is moved for measurement to the position shown in FIG. 3-3, and the reaction solution 102 is suctioned by the nozzle 109. In addition, the reagent vessels (a) 103, (b) 104 are moved in appropriate timing to the positions shown in FIGS. 3-5, 3-6, and the reagents (a) 105, (b) 106 are suctioned by the nozzle 109. After this, in order to remove sticking reaction solution 102 and reagents (a) 105, (b) 106 from the nozzle 109, the nozzle 109 is cleaned by moving the nozzle cleaning unit 201 in appropriate timing as shown in FIG. 3-4. There is a need to supply a new reagent (a) 105 to the reagent vessel (a) 103, and a new reagent (b) 106 to the reagent vessel (b) 104, in appropriate timing in order to avoid a shortage of the reagents (a) 105, (b) 106 consumed during the measurement. The present embodiment includes a reagent supply unit (a) 303 that supplies the reagent (a) 105 to the reagent vessel (a) 103, and a reagent supply unit (b) 304 that supplies the reagent (b) 106 to the reagent vessel (b) 104. In the present embodiment, the reagent (a) 105 is supplied at the position shown in FIG. 3-6, and the reagent (b) 106 at the position shown in FIG. 3-5.

Reagent supply quantities are calculated from the liquid level detected by a detection function for the liquid level in the reagent vessel, and from a cross-sectional area of the reagent vessel.

Figures 3, 4, 5:
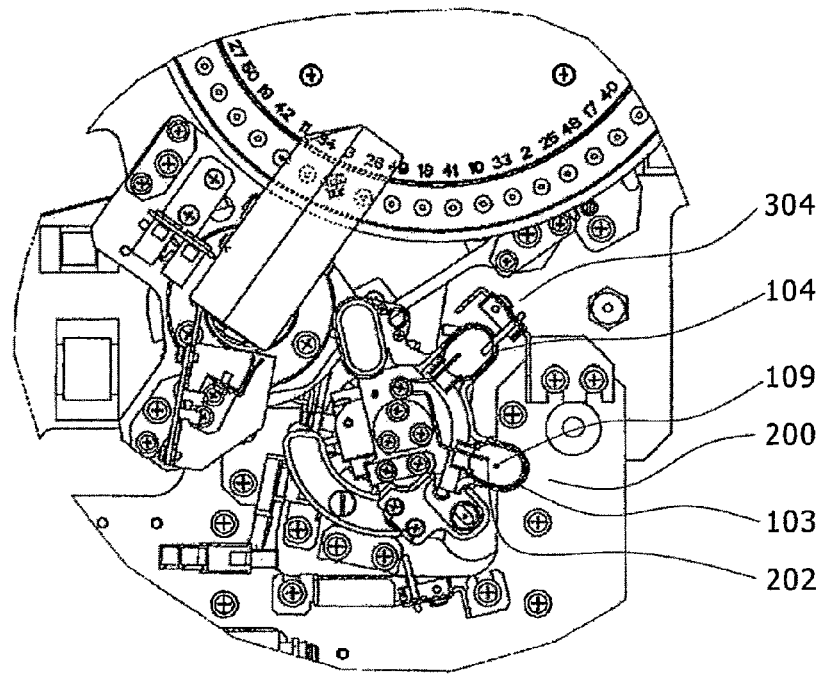
Figures 3, 4, 5, 6:
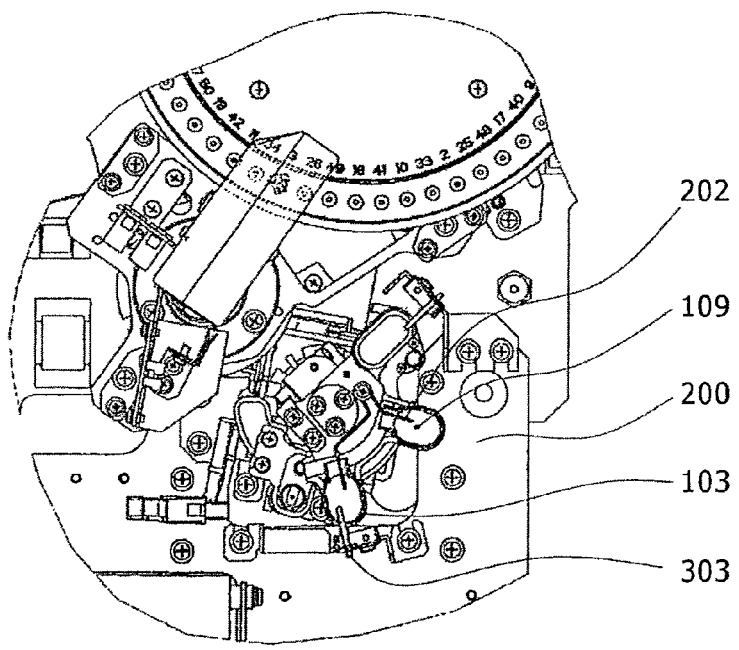
Figures 3, 4, 5, 6, 7:
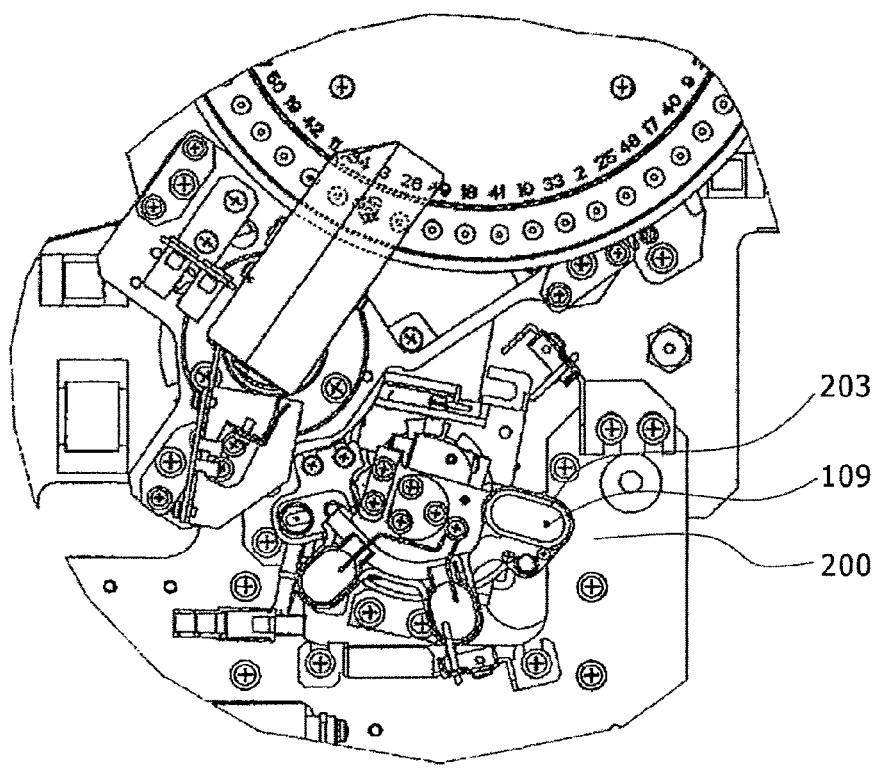

Known techniques for detecting the liquid level include, for example, the electrical continuity scheme for detecting electrical continuity when the nozzle or the like comes into contact with the surface of the liquid, and the capacitance scheme for detecting a change in capacitance when the nozzle or the like likewise comes into contact with the liquid surface. Ultrasonic detection and image-based detection are also known. In the present embodiment, the electrical continuity scheme is employed, in which scheme, an electroconductive electrode 202 is fixed to an electroconductive retainer 107 and has ends placed in the reagent vessel (a) 103, (b) 104. When the retainer 107 is moved upward, the nozzle 109 comes into contact with the liquid surface of the reagent (a) 105 in the reagent vessel (a) 103, as shown in FIG. 3-5, or with the liquid surface of the reagent (b) 106 in the reagent vessel (b) 104, as shown in FIG. 3-6. Continuity between the nozzle 109 and the retainer 107 then occurs to enable the detection of the liquid level. Using an electroconductive material to form the reagent vessels (a) 103, (b) 104 with which the electroconductive retainer 107 is in contact allows continuity to be detected without the electrode 202, if the nozzle 109 comes into contact with the liquid surface of the reagent (a) 105 or (b) 106. In addition, if actual reagent consumption is uniform, the liquid level detection function is not always required. Instead, it suffices just to provide an element that timely adds reagent according to the particular consumption.

In the present embodiment, analysis is conducted in the following order of steps, and at several stopping positions, a plurality of steps may be conducted at the same time for more efficient analysis: (1) Transport of the reaction vessel 101 (see FIG. 3-2)→(2) Suctioning of the reaction solution 102 (see FIG. 3-3)→(3) Cleaning of the nozzle 109 (see FIG. 3-4)→(4) Transport of the reaction vessel 101 (return to reaction disk)/Suctioning of the reagent (a) 105/Supply of the reagent (b) (see FIG. 3-1 or 3-5)→(5) Measurement→(6) Suctioning of the reagent (b) 106/supply of the reagent (a) (see FIG. 3-6)→(7) Suctioning of the reagent (a) 105 (see FIG. 3-5)→(1) Transport of the next reaction vessel 101 (see FIG. 3-2); subsequently, this sequence is repeated.

As described above, the retainer 107 in the reaction solution/reagent transport mechanism 200 of the present invention has a region in which to mount the cleaning liquid vessel 203 for holding the channel-cleaning liquid for the maintenance of the channel in the measuring unit. The channel in the measuring unit can also be cleaned by moving the reaction solution/reagent transport mechanism 200 to the position shown in FIG. 3-7, and then suctioning from the nozzle 109 the channel-cleaning liquid accommodated in the cleaning liquid vessel 203.

DESCRIPTION OF REFERENCE NUMERALS

100 Measuring unit
101 Reaction vessel
102 Reaction solution
103, 104 Reagent vessels
105, 106 Reagents
107 Retainer
108 Flow cell
109 Nozzle
110 Tube
111 Syringe
112 PMT (Photomultiplier)
200 Reaction solution/reagent transport mechanism
201 Nozzle cleaning unit
202 Electrode
203 Cleaning liquid vessel
300 Automated analyzer
301 Reaction disk
302 Reaction vessel transport unit
303, 304 Reagent supply units
401 Horizontal transport mechanism
402 Vertical transport mechanism

The invention claimed is:

1. An automated analyzer comprising:
   a first nozzle which sucks a reaction solution in a reaction vessel and one or more reagents in a plurality of reagent vessels, and whose location is fixed during analysis;
   a flow cell which is connected with the first nozzle and into which the reaction solution is sucked by the first nozzle;
   a detector which quantitatively detects a substance to be measured in the reaction solution sucked into the flow cell;
   a retainer having a plurality of mounting regions on which the reaction vessel that accommodates the reaction solution and the reagent vessels that accommodate the reagents necessary for the analysis are placed, respectively;
   a horizontal transport mechanism which rotationally or linearly moves the retainer in a horizontal plane to transport one of the mounting regions on which the reaction vessel or one of the reagent vessels is placed in accordance with a phase of the analysis to a first position below the first nozzle;
   a vertical transport mechanism coupled to the retainer and which moves the retainer in a vertical direction to transport the one of the mounting regions on which the reaction vessel or one of the reagent vessels is placed from the first position to a second position where the first nozzle sucks the reaction solution in the reaction vessel or the one of the reagents in the one of the reagent vessels.

2. The automated analyzer according to claim 1, wherein the first nozzle comprises a reagent quantity detector which detects a quantity of the one of the reagents in the one of the reagent vessels on the retainer.

3. The automated analyzer according to claim 1, further comprising:
   a reactor which accepts a plurality of reaction vessels that accommodate the reaction solution; and
   a gripper which transports the reaction vessel containing the reaction solution to be measured from the reactor to the retainer.

4. The automated analyzer according to claim 1, further comprising:
   a reaction vessel and a plurality of reagent vessels, wherein the reaction vessel and the plurality of reagent vessels are placed on a circumference of the retainer, and
   the horizontal driving motor revolves the retainer.

5. The automated analyzer according to claim 1, wherein a cleaning liquid vessel which accommodates a liquid to clean a channel from the first nozzle to the flow cell is placed on the retainer.

6. The automated analyzer according to claim 1, further comprising:
   a second nozzle which supplies the reagents to the reagent vessels placed on the retainer.

7. The automated analyzer according to claim 1, further comprising:
   a syringe which is connected to the flow cell to suck the reaction solution into the flow cell via the first nozzle.

8. The automated analyzer according to claim 6, further comprising:
   a syringe which is connected to the flow cell to suck the reaction solution into the flow cell via the first nozzle.

* * * * *